United States Patent
Ham et al.

(10) Patent No.: US 10,124,031 B2
(45) Date of Patent: Nov. 13, 2018

(54) COMPOSITION FOR PREVENTING ALZHEIMER'S DISEASE, CONTAINING PURPLE BAMBOO SALT, AND METHOD FOR PREPARING PURPLE BAMBOO SALT

(71) Applicant: Mokpo National University Industry-Academia Cooperation Group, Jeollanam-do (KR)

(72) Inventors: Kyung Sik Ham, Gwangju (KR); Jeong Yong Cho, Gwangju (KR); Promyo Kitiong, Jeollanam-do (KR); Sun Young Park, Jeollanam-do (KR); JinRui Zhu, Jeollanam-do (KR)

(73) Assignee: MOKPO NATIONAL UNIVERSITY INDUSTRY-ACADEMIA COOPERATION GROUP, Jeollanam-Do (KR)

( * ) Notice: Subject to any disclaimer, the term of this patent is extended or adjusted under 35 U.S.C. 154(b) by 243 days.

(21) Appl. No.: 14/443,259

(22) PCT Filed: Jan. 22, 2014

(86) PCT No.: PCT/KR2014/000609
§ 371 (c)(1),
(2) Date: May 15, 2015

(87) PCT Pub. No.: WO2014/116015
PCT Pub. Date: Jul. 31, 2014

(65) Prior Publication Data
US 2015/0297664 A1  Oct. 22, 2015

(30) Foreign Application Priority Data
Jan. 24, 2013  (KR) .................... 10-2013-0007827

(51) Int. Cl.
*A61K 36/899* (2006.01)
*A23L 27/00* (2016.01)
*A23L 33/105* (2016.01)

(52) U.S. Cl.
CPC ............ *A61K 36/899* (2013.01); *A23L 27/00* (2016.08); *A23L 33/105* (2016.08)

(58) Field of Classification Search
CPC .................................................. A61K 36/899
USPC ........................................................ 424/750
See application file for complete search history.

(56) References Cited

FOREIGN PATENT DOCUMENTS

| KR | 20110050649 B | * | 11/2012 | |
| KR | 10-2012-0132064 | | 12/2012 | ............. A61K 33/14 |
| KR | 20120134264 A | * | 12/2012 | |

OTHER PUBLICATIONS

Xuan, et al. (2012) "Hydrogen sulfide attenuates spatial memory impairment and hippocampal neuroinflammation in beta-amyloid rat model of Alzheimer's disease." *Journal of Neuroinflammation* 9:202, pp. 1-11.
International Search Report (ISR) dated Jul. 31, 2014 in PCT/KR2014/000609.

* cited by examiner

*Primary Examiner* — Christopher R Tate
*Assistant Examiner* — Deborah A Davis
(74) *Attorney, Agent, or Firm* — Harness, Dickey & Pierce, P.L.C.

(57) ABSTRACT

Provided is a functional composition for preventing an Alzheimer's disease, in which the composition includes heat-treated salt that is heat-treated at 800° C. to 1200° C. as an effective component and other pharmaceutically or sitologically acceptable components. The composition can prevent an Alzheimer's disease by effectively blocking the cause path of an Alzheimer's disease in a human body.

5 Claims, 10 Drawing Sheets

COMPOSITION FOR PREVENTING ALZHEIMER'S DISEASE, CONTAINING PURPLE BAMBOO SALT, AND METHOD FOR PREPARING PURPLE BAMBOO SALT

CROSS-REFERENCE TO RELATED APPLICATIONS

This application is a national phase application of PCT Application No. PCT/KR2014/000609, filed on 22 Jan. 2014, which claims benefit of Korean Patent Application 10-2013-0007827, filed on 24 Jan. 2013. The entire disclosure of the application identified in this paragraph is incorporated herein by reference.

TECHNICAL FIELD

The present invention relates to a functional composition for preventing dementia, such as, an Alzheimer's disease, which is a technique for the field of the prevention of disease, such as, dementia caused by the reduction of brain efficiency, and especially, can effectively block a biological path of inducing an Alzheimer's disease in a human body.

BACKGROUND

Today, a senile disorder is on the increase by drastically increasing the population of old people, and thus, it has become a social issue. Especially, there has been a huge increase of the disorders involved in the aging of cognitive function and neurodegenerative disorder, including metabolic syndromes, such as, diabetes, blood pressure disorders, and a stroke that are lifestyle diseases among senile disorders. Among them, the neurodegenerative disorder causes the problems in a cognitive function, a perception function, a sense function, and a physical intelligence ability due to the decrease and loss of the function of a brain cell, and as a main diseases, there are an Alzheimer's disease, a Parkinson's disease, and a Huntington's disease. Among them, the Alzheimer's disease is a cognitive dysfunction, the main symptom of senile dementia, and the fastest growing disease around the world. It is reported that as the main causative agent of the Alzheimer's disease, there are an amyloid beta aggregation, an acetylcholine content decrease, a neurofibrillary tangle formation, and the like. There are suggested that these diseases are concerned in heredity, environment, and life habit, but the cause of disease thereof is still unclear.

Salt is a very important component for a physiological function, such as, blood pressure regulation, nutrient transportation, and nerve transmission in a body. However, it is known that over-consumption of salt causes oxidative stress in the body and also influences metabolic syndromes, such as, diabetes and blood pressure disorders. Meanwhile, the contradictory result thereof is reported, in which the excessive restriction of salt consumption (5 g or less per a day) causes increased mortality rate by hyperlipidemia, metabolome deformation (renin and insulin resistant increase, the concentration changes of hormone, such as, aldosterone and noradrenalin, and the like), and cardiovascular disorders.

Our daily salt is largely classified into rock salt, solar salt, refined salt, and white salt. To date, there have been no studies about the effects of various types of salts on our health. Recently, it turned out that mineral-rich salt (solar salt) causes low oxidative stress and exhibits low occurrence of metabolic syndromes, such as, diabetes and blood pressure disorders as compared with general salt without mineral. Among various types of salts, in Korea, there are mineral-rich solar salt and processed salt, such as, roast bamboo salt, prepared by heating salt, which can help our health as compared with general salt without mineral. Among them, roast bamboo salt including purple bamboo salt is prepared by burning and melting Korean solar salt along with subsidiary material, such as, bamboo, at a high temperature, is only produced in Korea, is consumed for a long time, and has strong sulfur odor. From old times, slat has been widely used for treating inflammation, stomach ulcer, and diabetes, and recently, it has been confirmed by scientists that salt has biological activities, such as, antioxidative activity, anti-inflammation, anti-virus, or anti-cancer.

SUMMARY

Technical Problem

An object of the present invention is to provide a composition for preventing an Alzheimer's disease, in which the composition effectively blocks the cause path of Alzheimer' disease, and can be easily and continuously taken, generally.

Another object of the present invention is to provide a method for purple bamboo salt that is the effective component of the composition for preventing an Alzheimer's disease.

Technical Solution

The functional composition for preventing an Alzheimer's disease according to an embodiment of the present invention includes salt that is heat-treated at 800 to 1200° C. and a pharmaceutically or sitologically acceptable functional component.

The heat-treated salt may include purple bamboo salt, and the purple bamboo slat may be prepared by using solar salt.

The purple bamboo salt may produce at least 1400 µg of hydrogen sulfide per 1 g inside the body.

The method for preparing purple bamboo salt for preventing an Alzheimer's disease according to another embodiment of the present invention includes adding solar salt and a finely cut piece of bamboo in a heating furnace; heating the heating furnace at 800 to 1200° C. for 30 minutes to 2 hours; and cooling the heating furnace by maintaining the heating furnace at room temperature after completing the heating, in which the heating and cooling are repeated 3 to 5 times.

After cooling, the method further includes grinding the heat-treated solar salt. The solar salt and the finely cut piece of bamboo may be added in the rate of 4:1 to 1:1.

SUMMARY

By taking the purple bamboo salt for preventing an Alzheimer's disease according to an embodiment of the present invention, hydrogen sulfide that is known as a kind of gaseous transmitter is induced in the body to inhibit the production of Alzheimer's disease initiator or promote the production of Alzheimer's disease inhibitor, thereby effectively preventing an Alzheimer's disease.

In addition, the frequency of the outbreak of dementia-related disorders can be significantly reduced only by substituting general salt that should be continuously taken in the daily living with purple bamboo salt.

Furthermore, sodium chloride that is easily used for the conventional various food or medicines can be easily substituted with purple bamboo salt, and also, in the case where the purple bamboo salt is included in a food composition, the taste and flavor of food can be further increased.

Especially, when the purple bamboo salt is prepared by using solar salt as a raw material, in the case of taking the functional composition of the present invention, proper mineral is supplied in the human body, and thus, it can prevent an Alzheimer's disease that is an object of the present invention, and also, side effects in the human body due to the mineral lack can be reduced.

DETAILED DESCRIPTION

Figure 1:
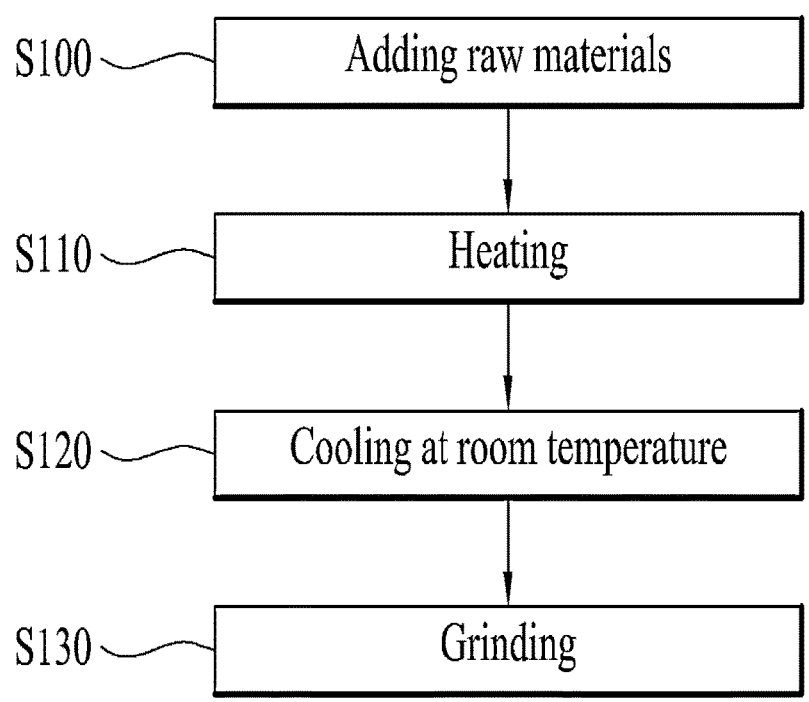
FIG. 1 is a flow chart illustrating the steps of preparing the purple bamboo salt according to other embodiment of the present invention.

Hereinafter, a composition for preventing an Alzheimer's disease, which includes the purple bamboo salt according to an embodiment of the present invention, and a method of preparing the purple bamboo salt, will be described in detail. However, the technical scope of the present invention is not limited to the description of the following Examples, and is only considered by claims to be described below.

The functional composition for preventing an Alzheimer's disease according to an embodiment of the present invention includes heat-treated salt that is heat-treated at 800° C. to 1200° C., and a pharmaceutically or sitologically acceptable functional component. The heat-treated salt is preferably heat-treated salt in a type of roast bamboo salt obtained by the process of preparing roast bamboo salt, including the heat-treated salt obtained through the heat treatment of general salt. Furthermore, the heat treated salt may include purple bamboo salt, and the purple bamboo salt may be prepared using solar salt. At this time, the solar salt means the salt prepared by evaporating moisture with natural wind and sunlight in a salt pond. The solar salt may include 75 to 95 wt % of sodium chloride, mineral, such as, calcium, potassium, and magnesium, or other salts. The purple bamboo salt may be prepared by repeating the heat treatment of the solar salt along with bamboo at 800° C. to 1200° C. The method of preparing purple bamboo salt will be described, hereinafter, in detail.

The purple bamboo salt may produce at least 1400 μg of hydrogen sulfide ($H_2S$) per 1 g inside the body. There is no hydrogen sulfide in non-processed solar salt, rock salt, and general salt. In the case of roast bamboo salt, the production amounts of hydrogen sulfide are different according to a type of roast bamboo salt. The excessive hydrogen sulfide is harmful to the human body. However, the small amount of hydrogen sulfide taken may play a role as gaseous transmitter, that is similar to NO and CO. Especially, the small amount of hydrogen sulfide has various physiological functions, such as, vasodilatation, anti-inflammation, anti-hypertension, intercellular signaling, dementia suppression, and anti-stomach ulcer effects, and thus, the hydrogen sulfide receives attention of many scientists. Especially, it is reported that among various physiological functions of hydrogen sulfide, it inhibits β-secretase (BACE) activity that is a factor of inducing neurogenic dementia, and thus, exhibits an effect on preventing an Alzheimer's disease.

The purple bamboo salt may be included as the effective component of food composition or medical composition, and according to an embodiment of the present invention, the food composition or medical composition is a composition capable of being introduced in the human body by the way of ingestion. Meanwhile, examples of the food may include the food that requires salt, such as, liquid beverage, and snacks or seasoning. Especially, when the purple bamboo salt is applied for a food composition that is generally used like seasoning, the effect on preventing an Alzheimer's disease may be strengthened by the continuous ingestion of purple bamboo salt. In addition, it is ultimately possible to prevent the outbreak of senile dementia by preventing an Alzheimer's disease that is one of the main causes of dementia.

FIG. 1 is a flow chart illustrating the steps of preparing the purple bamboo salt according to other embodiment of the present invention.

Referring to FIG. 1, the method for preparing purple bamboo salt for preventing an Alzheimer's disease according to other embodiment of the present invention includes adding solar salt and a finely cut piece of bamboo in a heating furnace (S100); heating the heating furnace (S110); and cooling the heating furnace by maintaining the heating furnace at room temperature after completing the heating (S120). In addition, the heating and cooling are preferably repeated 3 to 5 times. As the heating furnace, the container that is heat-resistant and has high transfer rate, such as, ceramic, may be used. The heating furnace may be preferably sealed so as not to be mixed with outer air during heating. A type of the heating furnace is not particularly limited, but the heating furnace preferably is cylindrical so as to transfer heat inside the furnace and stand heat. The bamboo is a generic term used to describe a evergreen perennial plant belonging to a monocotyledon graminales graminae bamboo plant, and 2 to 4-year bamboo may be used. Over a week after cutting the bamboo, the sap of bamboo is lack, and thus, the bamboo immediately after being cut is preferably used. The bamboo is preferably used in a type of finely cut piece so as for the components of bamboo to be sufficiently discharged in the heating (S110) and then to be absorbed into the solar salt. The solar salt and finely cut piece of bamboo may be added in the rate of 4:1 to 1:1. When the bamboo is excessively added, the amount of ashes produced is too many, and also, the ashes are included in purple bamboo salt. Therefore, the good purple bamboo salt may not be prepared. When the bamboo is heated along with the solar salt, the bamboo is totally burn to be absorbed into the solar salt, and thus, the purple bamboo salt in a type of lump is remained.

The heating (S110) may be performed at 800° C. to 1200° C. for 30 minutes to 2 hours, and preferably 850° C. to 1100° C. for 50 minutes to 90 minutes. When the heating is performed at less than 800° C. or is performed for less than 30 minutes, purple bamboo salt may not be formed. When the heating is performed at 1200° C. or more, it is not preferable in terms of cost and efficiency, and also, the production of hydrogen sulfide from the purple bamboo salt may be significantly reduced.

The cooling (S120) may be performed by maintaining the heating furnace at room temperature after completing the heating (S110). When quickly cooling using a cooler, the crystals of the purple bamboo salt may be too coarse, and thus, the cooling is performed at room temperature, 15° C. to 25° C.

In order to repeat the heating (S110) and the cooling (S120), the grinding of solar salt (S130) may be further included after the cooling (S120). Since the heated solar salt is easily broken, the method of grinding is not particularly limited.

Hereinafter, the present invention will be described in more detail with reference to Examples. However, the following Examples are not limited to the technical scope of the present invention.

EXAMPLES

Preparation of Purple Bamboo Salt

Solar salt produced in Sinan-gun, Jeollanam-do and the finely cut piece (2×2 cm) of 2-year bamboo were added in the weight rate of 2:1 to a ceramic heating furnace. The ceramic heating furnace was heated at 850° C. for 1 hour. After opening the heating furnace after completing the heating, the salt inside the furnace was ground into a type of coarse particle. Since then, the above process was repeated three times to prepare purple bamboo salt.

Experiments

Test 1: Confirmation of Content of Hydrogen Sulfide Produced in Purple Bamboo Salt The corresponding amounts of hydrogen sulfide in the purple bamboo salt and general salt (Sigma-Aldrich) without mineral was investigated. 100 g of each of the purple bamboo salt and general salt was dissolved in 1 L of distilled water, and then, centrifuged for 2 minutes to remove insoluble substances to prepare a sample solution. 430 µL of each of the prepared sample solutions was mixed with 50 µL of saline solution. 250 µL of 1% zinc acetate solution and 250 µL of distilled water were added thereto; then, 133 µL of 20 mM N,N-dimethyl-p-phenylendediamine sulfate solution dissolved in 7.2 M HCl solution and 133 µL of 30 mM $FeCl_3$ dissolved in 1.2 M HCl solution were added; the mixture thus obtained was reacted for 5 minutes. For the reaction solution thus obtained, absorbance at 670 nm was measured using a 96 well microplate reader. In addition, a standard curve was plotted with standard substance NaHS (3.125-200 µM), and then, the content of hydrogen sulfide produced from salt was obtained using the standard curve.

Figure 2:
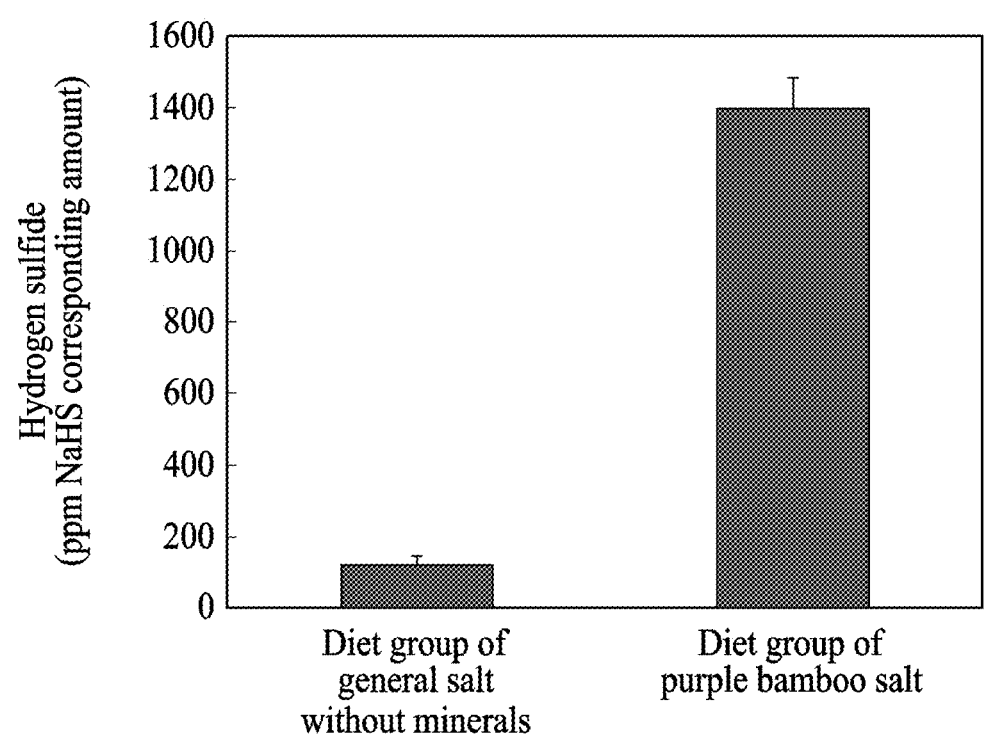
FIG. 2 is a graph illustrating the comparison between the contents of hydrogen sulfides, which are produced from the purple bamboo salt according to an embodiment of the present invention and general salt.

FIG. 2 is a graph illustrating the comparison between the contents of hydrogen sulfides, which are produced from the purple bamboo salt according to an embodiment of the present invention and general salt.

Referring to FIG. 2, it was confirmed that while the small amount of hydrogen sulfide was detected in general salt, the great deal of hydrogen sulfide was detected in the purple bamboo salt. At this time, the production amount of hydrogen sulfide per 1 g of the purple bamboo salt was 1466 µg.

Test 2: Animal Experiment for Confirming Effect of Purple Bamboo Salt on Preventing Alzheimer's Disease As the feed used in the animal experiments of the present test, a general feed was prepared based on AIN-93G, and each of the feed was prepared by adjusting the content of 8% (w/w) NaCl with the salt used in TEST 1. The group that was treated with general salt without mineral and the group that was treated with purple bamboo salt (PBS) were used as the experimental groups.

The experimental animals used for the present invention were 4-week normal rats (Male Sprague-Dawley rats, 120 to 130 g of body weight, purchased from Damul Science). The normal rats were accommodated in a breeding room set with a relative humidity of 55±5%, a temperature of 25±1° C., and 12 h light-dark cycle for 1 week with general feed, and then, the weights thereof were measured. Since then, each of the experimental groups was divided into n=8 by the randomized block. The rats were fed with the feeds including general salt and purple bamboo salt for 11 weeks, and the rats ate freely water and diet.

The experimental animals were fasted for 12 hours before being sacrificed, and then, were anesthetized with ether. Since then, the animals were sacrificed by cutting the heads thereof with a cutter. The brain tissues were isolated from the obtained heads using a Guillotine method. The isolated whole brains were immediately stored in a deep freezer of −80° C., and then, were used for the experiments.

Test 2-1: Confirmation of Effect of Purple Bamboo Salt on Preventing Alzheimer's Disease Through Animal Test 1) Confirmation of Effect of Purple Bamboo Salt on Suppressing Amyloid Beta Production Using the brain tissues of the normal rats ingested with purple bamboo salt and general salt as an object, the contents of Aβ1-40 and Aβ1-42 that were amyloid beta products were measured using Wako Human/rat amyloid 1-40 and 1-42 ELISA kits. The protein solution (100 µL) obtained from each of the brain tissues was applied to each of ELISA Kit, and then, was reacted at 4° C. for 12 hours. The supernatant was removed therefrom, and then washed. 100 µl of HRP-conjugated antibody solution was added in the reaction kit, the reaction solution thus obtained was reacted at 4° C. for 1 to 2 hours, and then, the antibody solution was removed and washed. 100 µl of TMB solution was added into the washed kit, and then, reacted at room temperature and dark condition for 30 minutes. 100 µl of stop solution was added into the reaction kit, and then, the absorbance at 450 nm was measured using a microplate reader. The contents of Aβ1-40 and Aβ1-42 in the brain tissue of the sample group was obtained with a standard curve prepared by using a standard substance [Aβ1-40 (1-100 pmol/l) and Aβ1-42 (0.1-20 pmol/l)].

Figure 3:
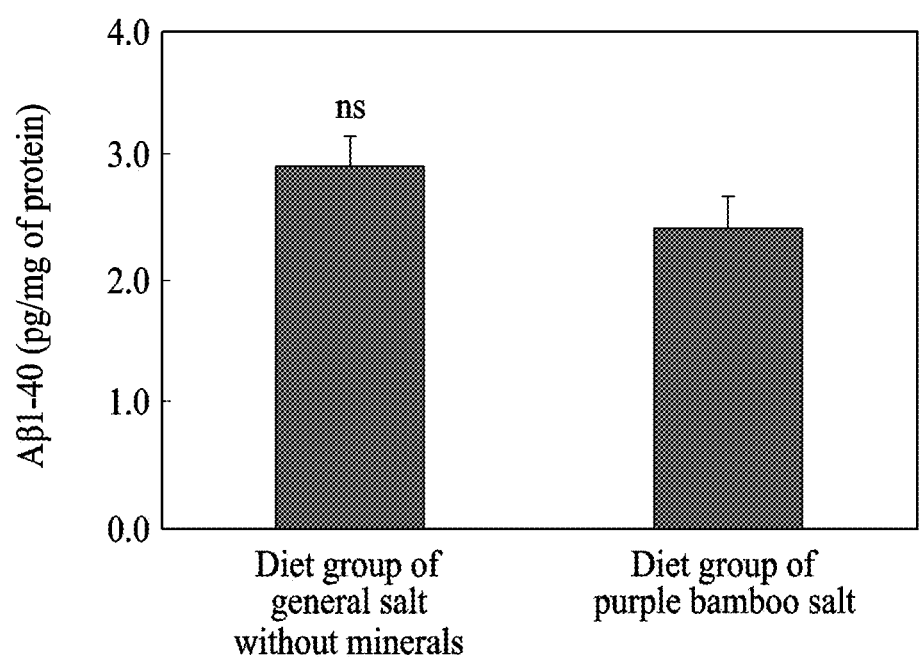
FIG. 3 is a graph illustrating the comparison between the production amounts of Aβ1-40s that are amyloid beta products in the diet group of the purple bamboo salt according to an embodiment of the present invention and the diet group of the general salt.

FIG. 3 is a graph illustrating the comparison between the production amounts of Aβ1-40s that are amyloid beta products in the diet group of the purple bamboo salt according to an embodiment of the present invention and the diet group of the general salt.

Figure 4:
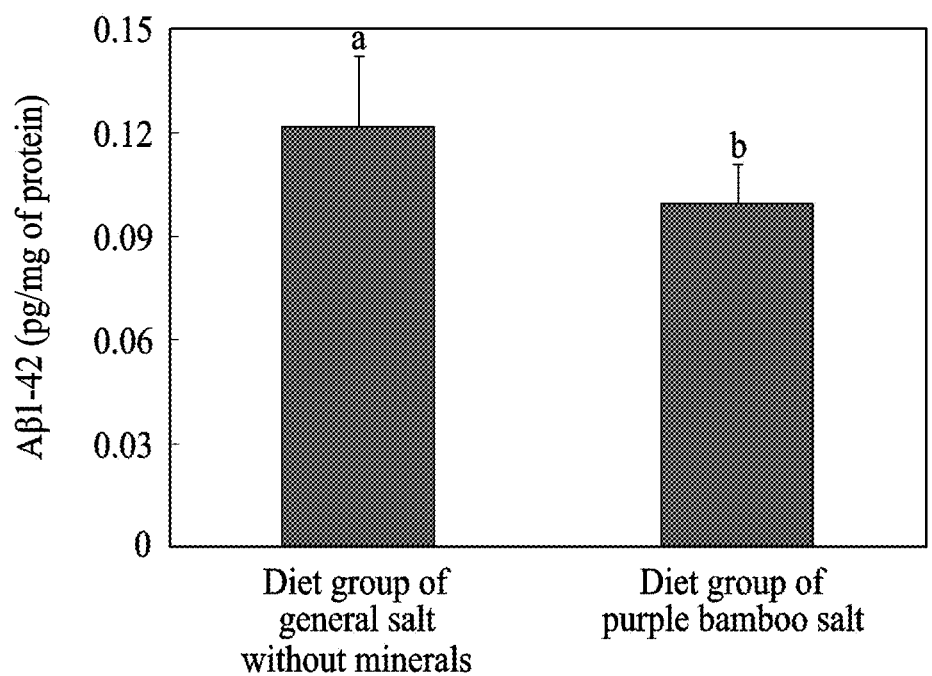
FIG. 4 is a graph illustrating the comparison between the production amounts of Aβ1-42s that are amyloid beta products in the diet group of the purple bamboo salt according to an embodiment of the present invention and the diet group of the general salt.

Referring to FIG. 3, the graph exhibited the effect of the purple bamboo salt according to an embodiment of the present invention on decreasing the production of Aβ1-42 that was an amyloid beta product. As illustrated in FIGS. 3 and 4, in the case of Aβ1-40 in the brain, the diet group of the purple bamboo salt exhibited low content as compared with the general salt without mineral, but there was no significant difference between two diet groups (P<0.05). In the case of Aβ1-42, the diet group of the purple bamboo salt exhibited the significantly low content as compared with the general salt without minerals (P<0.05).

The amyloid beta was produced by decomposing an amyloid precursor protein (APPP) that was a membrane receptor protein by the action of β-secretase (BACE1) and γ-sceretase. As the products thereof, Aβ1-40 was produced the most and Aβ1-42 was produced in the amount of about 10%. Among them, it was known that Aβ1-42 exhibited hydrophobic property, and thus, the amyloid beta polymer was well formed and also the toxicity thereof was strong. It was confirmed that as compared with general salt without minerals, the purple bamboo salt had the effect on decreasing the production of Aβ1-42 that was allowed to form the amyloid beta aggregation, well.

2) Confirmation of Effect of Purple Bamboo Salt on Regulating Factor Involved in Removing or Producing Amyloid Beta With the brain tissues of normal rats that were ingested with each of purple bamboo salt and general salt, the expression amounts of the factors involved in producing and removing amyloid beta, which were typical factors involved in the cause of an Alzheimer's disease were measured by a western blotting. 1 ml of lysis buffer prepared by using 0.05% triton x-10, 0.2 M HEPES (pH 7.4), 0.01M NaF, 0.01M EDTA (pH 7.4), 2 mM phenylmethylsulfonyl fluoride, 0.01M sodium pyrophosphate, 1 μg/ml of pepstain, 1 μg/ml leupeptin, and 0.1 μg/ml of aprotin was added to the whole brain tissue (0.3 g), and then, the brain tissue in the buffer was homogenized in an ice with Polytron (PT1200E, Kinematicca AG). The homogenized solution was slowly stirred at 4° C. for 1 hour, and then, was centrifuged at 15,000×g and 4° C. for 20 minutes to obtain the supernatant. The protein content in each of the treatment groups was measured with a Bradford method. 10 μL of 2× tricine sample buffer (Biorad) was added to the same protein solution (100 μg, 10 μL) to each of the diet groups to perform the denaturation of the protein at 95° C. for 5 minutes. Since then, the solution was subjected to sodium dodecyl sulfate-polyacrylamide gel electrophoresis (SDS-PAGE). The separated proteins were transferred into a polyvinylidene fluoride (PVDF) membrane I, and then, the membrane was washed with tris-buffer-saline, and then, was subjected to a blocking with 0.05% Tween-20 (TBST) buffer including 3% bovine serum albumin (BSA). Since then, the membrane was washed with a TBST solution three times for 5 minutes, respectively, and then, was added into a lyophilized buffer including primary antibody. Since then, the membrane was reacted at room temperature while being slowly stirred. The membrane after completing the reaction with primary antibody was washed with a TBST solution three times for 5 minutes, respectively; then, horseradish peroxidase HRP-conjugated goat anti-rabbit immunoglobulin G was added thereto; and then, the reaction was performed at room temperature for 1 hour. Since then, the washed membrane was reacted with an ECL (enhanced chemiluminescence) solution including luminal. As a primary antibody, the lyophilized buffer that was diluted with each of BACE1 (1:1,000), LRP1 (1:1,000), RAGE (1:1,000), NEP (1:1,000), IDE (1:1,000), beta actin (1:1,000), and GPADH (1:1,000) was used.

Figure 5:
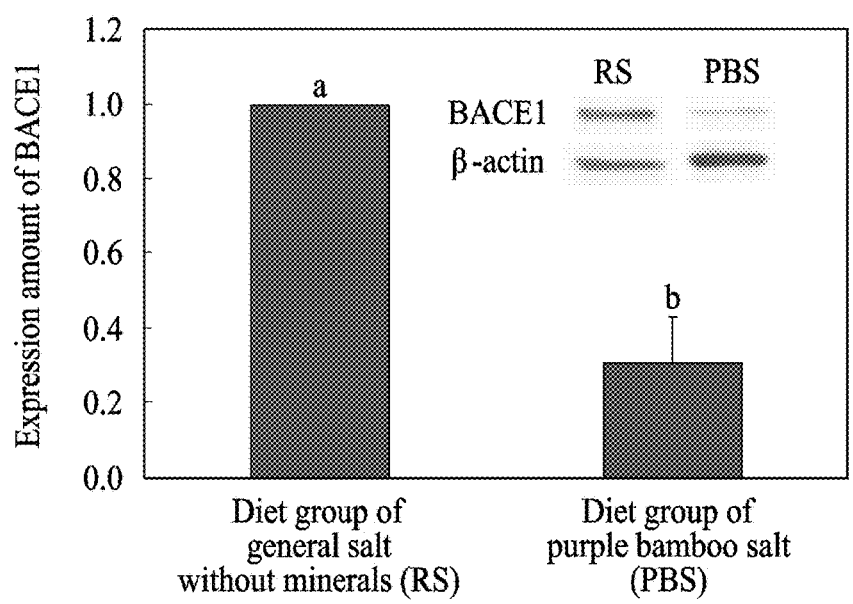
FIG. 5 is a graph illustrating the comparison between the expression amounts of BACE1s involved in amyloid beta products in the diet group of the purple bamboo salt according to an embodiment of the present invention and the diet group of the general salt.

FIG. 5 is a graph illustrating the comparison between the expression amounts of BACE1s involved in amyloid beta products in the diet group of the purple bamboo salt according to an embodiment of the present invention and the diet group of the general salt.

Referring to FIG. 5, it could be confirmed that the purple bamboo salt according to an embodiment of the present invention had the effect on suppressing the expression of BACE1 involved in the production of amyloid beta. The diet group of the purple bamboo salt exhibited significantly low expression amount of BACE1 as compared with the diet group of the general salt (P<0.05). The BACE1 produced amyloid beta that was a typical factor involved in the cause of Alzheimer's disease by decomposing an amyloid precursor protein (APP) that was a membrane receptor protein in a brain nerve cell. It was known that hydrogen sulfide suppresses the production of amyloid bête by inhibiting the expression of BACE1. It was confirmed that the purple bamboo salt included the great amount of substance producing hydrogen sulfide, and also, as compared with general salt without minerals, the purple bamboo salt suppressed the expression of BACE1. Therefore, it could be expected that there was a possibility that hydrogen sulfide produced from the purple bamboo salt was an important active substance of suppressing the expression of BACE1.

Figure 6:
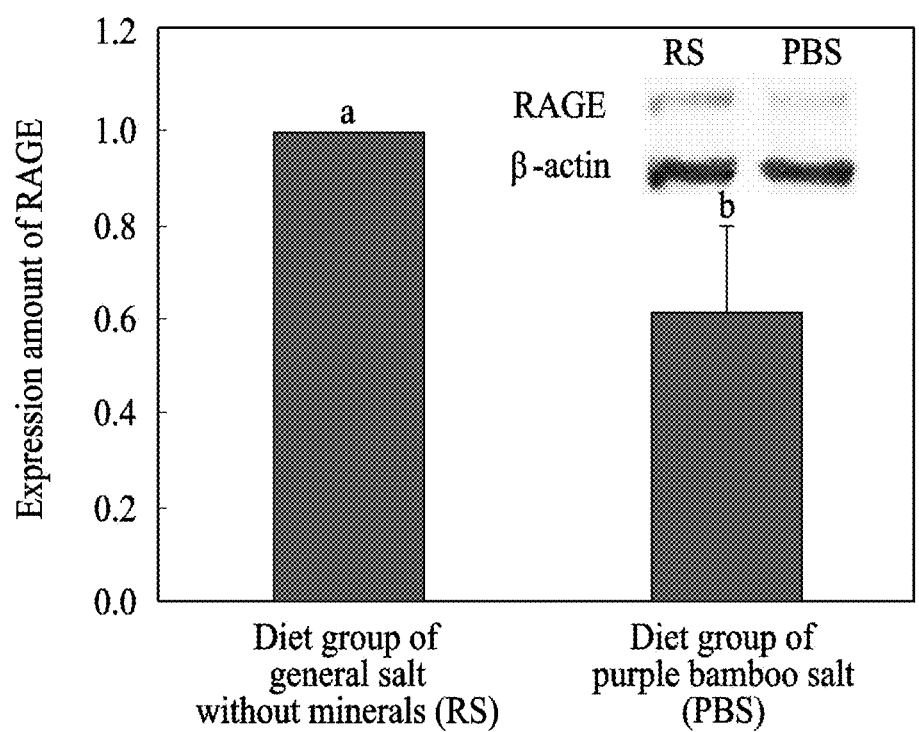
FIG. 6 is a graph illustrating the comparison between the expression amounts of RAGEs involved in removing amyloid beta products in the diet group of the purple bamboo salt according to an embodiment of the present invention and the diet group of the general salt.

FIG. 6 is a graph illustrating the comparison between the expression amounts of RAGEs involved in removing amyloid beta products in the diet group of the purple bamboo salt according to an embodiment of the present invention and the diet group of the general salt.

Referring to FIG. 6, it could be confirmed that the purple bamboo salt according to an embodiment of the present invention had the effect on suppressing the expression of RAGE (receptor for advanced glycation end products) involved in removing amyloid beta. FIG. 6 was the graph illustrating the effect of the purple bamboo salt according to an embodiment of the present invention on increasing the expression of Low density lipoprotein receptor related protein 1 (LRP1) involved in removing amyloid beta. As compared with the diet group of general salt, the diet group of the purple bamboo salt exhibited significantly low RAGE expression amount (P<0.05). It was known that RAGE is a protein of moving amyloid beta being present in blood into a brain tissue, and when advanced glycation end products and amyloid beta were increased in blood, the expression amounts thereof were increased in cerebrovascular and nerve cells, and also, they cause the oxidative damage and inflammation of a cell. Therefore, from the low expression amount of RAGE in the brain tissue in the diet group of the purple bamboo salt, it could be accepted that when the purple bamboo salt was ingested, the oxidative stress and inflammation reaction were decreased in blood vessel to produce the small amount of amyloid beta and advanced glycation end products, thereby decreasing the expression amount of RAGE. Therefore, it was a strong suggestion of the possibility that the oxidative stress and inflammation were also low even in erebrovascular, nerve cells, and brain cells. It could be confirmed that the purple bamboo salt according to an embodiment of the present invention had the effect on suppressing the expression of RAGE as compared with the general salt.

Figure 7:
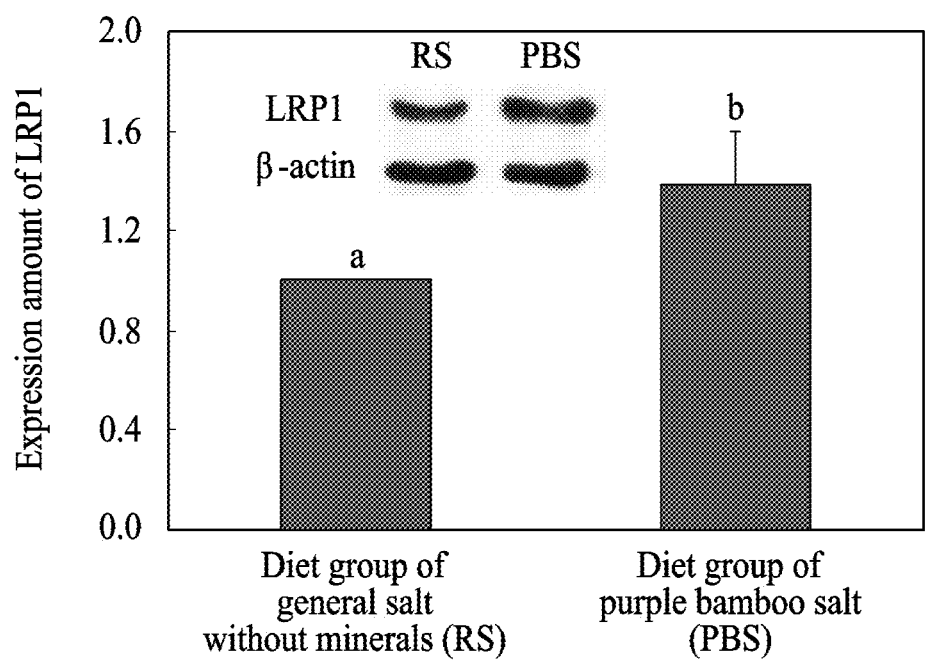
FIG. 7 is a graph illustrating the comparison between the expression amounts of LRP1s involved in removing amyloid beta products in the diet group of the purple bamboo salt according to an embodiment of the present invention and the diet group of the general salt.

FIG. 7 is a graph illustrating the comparison between the expression amounts of LRP1s involved in removing amyloid beta products in the diet group of the purple bamboo salt according to an embodiment of the present invention and the diet group of the general salt.

Referring to FIG. 7, the diet group of the purple bamboo salt exhibited significant high LRP1 expression amount as compared with the diet group of the general salt (P<0.05). It was known that LRP1 was an important receptor involved in the first step of removing amyloid beta from a brain tissue in a blood-brain barrier. Therefore, it could be confirmed that the purple bamboo salt had the effect on decreasing the amount of amyloid beta in a brain tissue by removing amyloid beta into the outside of brain tissue through increasing the expression amount of LRP1 in the blood-brain barrier, as compared with the general salt.

Test 2-2: Confirmation of Effect of Purple Bamboo Salt on Suppressing Oxidative Stress 1) Effect of Purple Bamboo Salt on Suppressing Oxidative Stress The contents of protein carbonyl were measured in the brain tissues of normal rats that were ingested with the purple bamboo salt and general salt. Using the same method as the method disclosed in the western blotting, 100 μL of 2 M HCl solution including 10 mM DNPH was added to 2 mg of the protein obtained from the brain tissue, and then, the solution thus obtained was reacted at room temperature and a dark room for 1 hour. At this time, the solution was stirred at 15-minute intervals. 1 mL of 10% trichloroacetic acid (w/v) that was cooled with an ice was added into the reaction solution, and then, the reaction solution was mixed. Since then, the reaction solution thus obtained was centrifuged at 3000×g for 10 minutes. The obtained protein pellet was repeatedly washed with 2 mL of ethanol/ethyl acetate (1:1, v/v) three times. Since then, the washed pellet was dissolved in 1.5 mL of 6 M guanidine HCl (pH 2.3), and then, reacted at 37° C. for 10 minutes. Since then, the absorbance thereof was measured at 370 nm. A molar extinction coefficient ($\varepsilon=2.2\times10^4$/cm M) of DNPH to the absorbance value was divided, and then, converted into the protein carbonyl content of the brain tissue.

Figure 8:
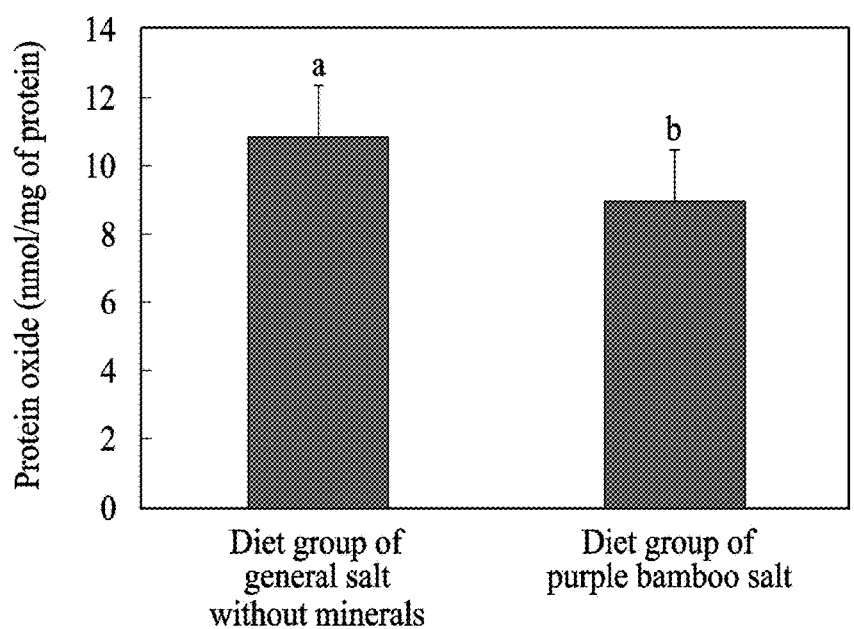
FIG. 8 is a graph illustrating the comparison between the production amounts of protein carbonyls in brain tissues in the diet group of the purple bamboo salt according to an embodiment of the present invention and the diet group of the general salt.

FIG. 8 is a graph illustrating the comparison between the production amounts of protein carbonyls in brain tissues in the diet group of the purple bamboo salt according to an embodiment of the present invention and the diet group of the general salt.

Referring to FIG. 8, the diet group of the purple bamboo salt (RBS) exhibited significantly low protein carbonyl content as compared with the diet group of the general salt (RS). It was known that the excessive salt ingestion influenced the oxidative stress in our bodies. According to the prior arts by the present inventors, the present inventors revealed that the purple bamboo salt exhibited low protein carbonyl content in the muscle tissue or fat tissue of the normal rats that were ingested with high salt, as compared with mineral-rich solar salt. It was again confirmed that the purple bamboo salt exhibited low oxidative stress even in the brain tissue as compared with the salt without minerals.

2) Effect of Purple Bamboo Salt on Suppressing the Production of TNF-α

Using the brain tissues of the normal rats that were ingested with the purple bamboo salt and general salt as an object, the contents of TNF-α were measured using ELISA kit for rat TNF-α (KOMA BIOTECH INC.). With the same method as the western blotting performed in the above experiments, the protein solution (100 μL) obtained from each of the brain tissues was added into each of the ELISA kits, the protein solution thus obtained was reacted at 4° C. for 2 hours, and then, the solution was removed and then washed. Since then, 100 μl of the antibody (0.1 μg/ml) solution was added to the reaction kit, the reaction was performed at room temperature for 2 hours, and then, the antibody solution was removed and washed. 100 μl of a colorimetric solution was added into the kit, and then, the reaction was performed at room temperature for 30 minutes. 100 μl of a stop solution was added into the reaction kit, and the absorbance thereof was measured at 450 nm using a microplate reader. The contents of TNF-α in the brain tissues of the diet groups were obtained using a standard curve prepared by using a standard substance [Aβ1-40 (62.5-4,000 μg/ml)].

Figure 9:
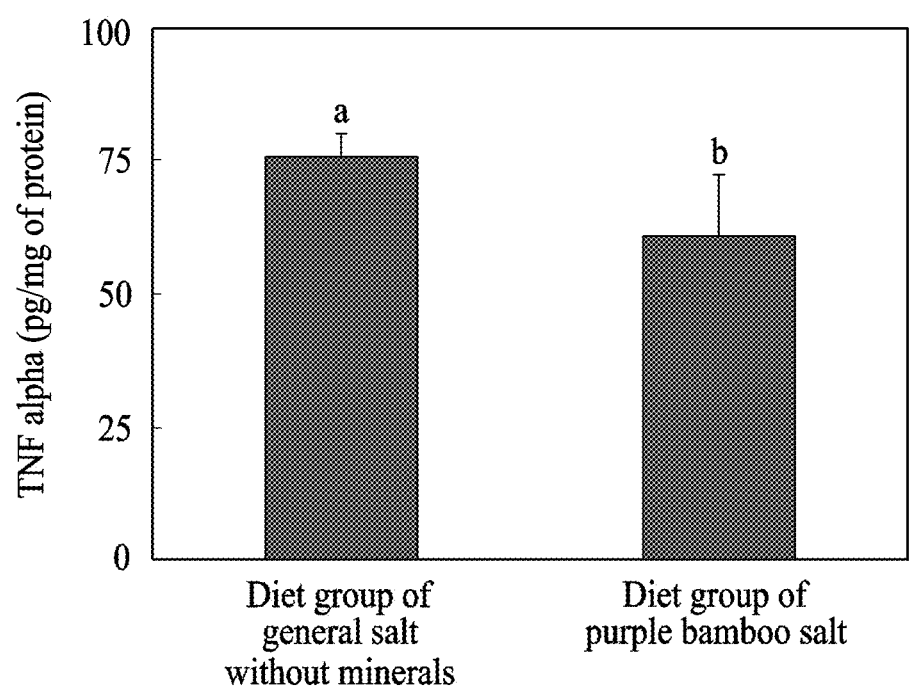
FIG. 9 is a graph illustrating the comparison between the production amounts of TNF-α in brain tissues in the diet group of the purple bamboo salt according to an embodiment of the present invention and the diet group of the general salt.

FIG. 9 is a graph illustrating the comparison between the production amounts of TNF-α in brain tissues in the diet group of the purple bamboo salt according to an embodiment of the present invention and the diet group of the general salt.

Referring to FIG. 9, the diet group of the purple bamboo salt exhibited significantly low content of TNF-α as compared with the diet group of the general salt (P<0.05). It was confirmed that the purple bamboo salt exhibited low oxidative stress and inflammation reaction as compared with salt without minerals.

3) Effect of Purple Bamboo Salt on Suppressing Expression of NF-κB p65

The NF-κB p65 in the brain tissues of the normal rats that were ingested with the purple bamboo salt and the general salt was measured with a western blotting. The productions of NF-κB p65 was measured with the same method as the method suggested in the test for confirming the effect of the purple bamboo salt on regulating factors involved in producing or removing amyloid beta. The primary antibody of NF-κB p65 was diluted with a lyophilized buffer in the rate of 1:1,000, and then, used.

Figure 10:
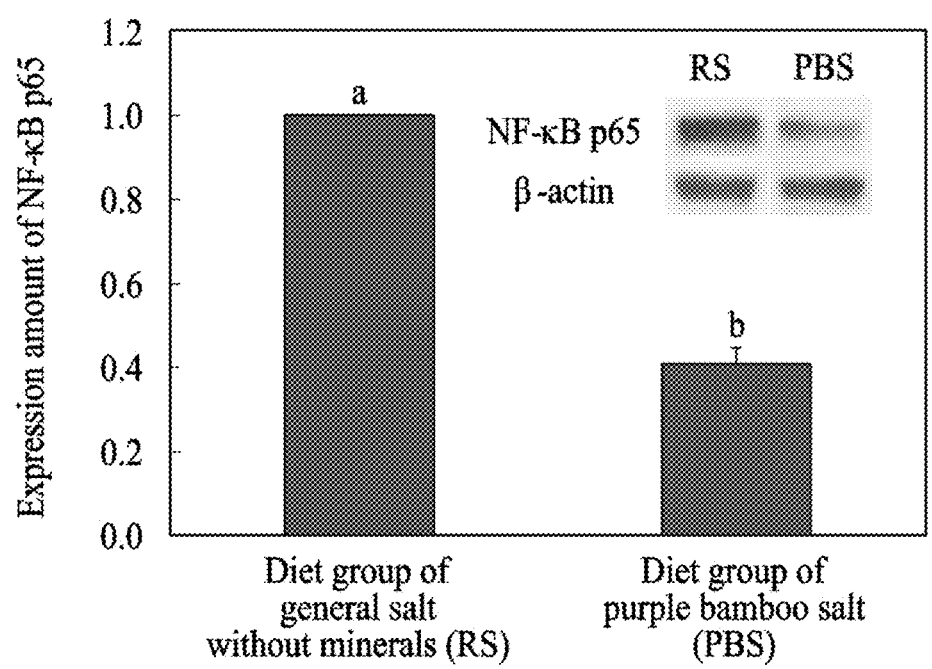
FIG. 10 is a graph illustrating the comparison between the expression amounts of NF-κB p65 involved in oxidative stress and inflammation reaction in the diet group of the purple bamboo salt according to an embodiment of the present invention and the diet group of the general salt.

FIG. 10 is a graph illustrating the comparison between the expression amounts of NF-κB p65 involved in oxidative stress and inflammation reaction in the diet group of the purple bamboo salt according to an embodiment of the present invention and the diet group of the general salt.

Referring to FIG. 10, as suggested above, the diet group of the purple bamboo salt (PBS) exhibited significantly low expression amount of NF-κB p65 as compared with the diet group of the general salt (RS). It was again confirmed that the purple bamboo salt exhibited low oxidative stress and inflammation reaction even in the brain tissue as compared with salt without minerals.

What is claimed is:

1. A method for decreasing in a mammal in need thereof aβ1-42, comprising:

administering to the mammal an effective amount of a composition comprising purple bamboo salt and a pharmaceutically or sitologically acceptable component, wherein the purple bamboo salt is a mineral-rich salt and produces at least 1400 µg of hydrogen sulfide per 1 g inside the body.

2. The method of claim 1, wherein the method is to reduce the risk of developing dementia or Alzheimer's disease.

3. The method of claim 2, wherein the purple bamboo salt has been heat-treated at 800° C. to 1200° C.

4. The method of claim 3, wherein the heat-treated salt includes purple bamboo salt.

5. The method of claim 4, wherein the purple bamboo salt has been prepared using solar salt.

* * * * *